US00RE34879E

United States Patent [19]

Bocchi et al.

[11] E Patent Number: Re. 34,879

[45] Reissued Date of Patent: Mar. 14, 1995

[54] IMPLANTABLE N-PHASIC DEFIBRILLATOR OUTPUT BRIDGE CIRCUIT

[75] Inventors: David E. Bocchi, Vadnais Heights; Jeffrey T. Laackman, Isanti; Stanley M. Bach, Jr., Shoreview, all of Minn.

[73] Assignee: Cardiac Pacemakers, Inc., St. Paul, Minn.

[21] Appl. No.: 51,899

[22] Filed: Mar. 12, 1993

Related U.S. Patent Documents

Reissue of:

[64] Patent No.: 4,998,531
Issued: Mar. 12, 1991
Appl. No.: 501,527
Filed: Mar. 28, 1990

[51] Int. Cl.[6] ..... A61N 1/39
[52] U.S. Cl. ..... 607/5
[58] Field of Search ..... 607/4, 5, 6, 7

[56] References Cited

U.S. PATENT DOCUMENTS 4,504,773 3/1985 Suzuki et al. .
4,693,253 9/1987 Adams .
4,840,177 6/1989 Charbonnier et al. .
4,850,357 7/1989 Bach, Jr. .

*Primary Examiner*—William E. Kamm
*Assistant Examiner*—George Manuel
*Attorney, Agent, or Firm*—Keck, Mahin & Cate

[57] ABSTRACT

An output bridge circuit comprising four independently controlled transistors connected between first and second electrode terminals and a defibrillation capacitor. Two of the four transistors are driven by push-pull driver circuits and connected between the capacitor and the first and second electrode terminals. The remaining two transistors are connected between the first and second electrode terminals and ground terminals. By triggering one of the transistors connected to the push-pull driver circuits and one of the transistors connected between the electrode terminals and the ground terminal, a mono-phasic, multi-phasic, or sequential defibrillation pulse can be generated by activating the appropriate transistors.

5 Claims, 6 Drawing Sheets

IMPLANTABLE N-PHASIC DEFIBRILLATOR OUTPUT BRIDGE CIRCUIT

Matter enclosed in heavy brackets [ ] appears in the original patent but forms no part of this reissue specification; matter printed in italics indicates the additions made by reissue.

BACKGROUND OF THE INVENTION

The present invention relates to an implantable defibrillator output circuit, and more specifically to an output bridge circuit for issuing mono-phasic, multi-phasic, and sequential defibrillation pulses.

In the field of implantable defibrillators, it has been found that a bi-phasic defibrillation pulse applied to a fibrillating heart is useful in controlling and arresting ventricular fibrillation. See for example, commonly assigned U.S. patent application Ser. No. 143,061, filed Jan. 12, 1988, and entitled BI-PHASIC PULSE GENERATOR FOR AN IMPLANTABLE DEFIBRILLATOR. This application discloses a circuit for generating a bi-phasic voltage pulse, the circuit including first and second thyristors for regulating the voltage of a capacitor. The circuit further includes an output sensing section for sensing the exponential decay of the capacitor and signalling a control circuit to switch metal oxide silicon insulated gate transistors (MOSIGT) in a ground circuit such that after one thyristor applies a voltage pulse to the heart in a first polarity the control circuit interrupts to turn off the thyristor. The other thyristor then applies the voltage pulse to the heart in a second and opposite polarity. It, in turn, is turned off by a second MOSIGT. While this disclosed circuit is capable of generating a bi-phasic defibrillation pulse, the ground return terminal needs to be disconnected in order to commutate the current flow through the electrodes to the heart.

SUMMARY OF THE INVENTION

It is a primary object of the present invention to provide an implantable defibrillator output circuit capable of delivering a multi-phasic defibrillation pulse without having to repeatedly disconnect the ground return reference terminal.

It is another object of this invention to provide an implantable defibrillator output bridge circuit wherein energy on a defibrillator capacitor can be used for the delivery of bi-phasic, tri-phasic, and sequential defibrillation pulses.

The present invention comprises an implantable defibrillator output circuit comprising a bridge configuration having four Metal Oxide Silicon Insulated Gate Transistors (MOSIGT's) and arranged with the top two transistors having transformer isolated gate drives and the bottom two transistors having turn off time control and low impedance clamping. Furthermore, all four MOSIGT's have independent on/off control to allow for mono-phasic, bi-phasic, tri-phasic, and sequential defibrillation pulses, and permit the selection of delivery polarity as either positive or negative without having to disconnect the ground return reference.

The above and other objects and advantages will become more readily apparent when reference is made to the following description taken in conjunction with the accompanying drawings.

DETAILED DESCRIPTION OF THE DRAWINGS

Figure 1:
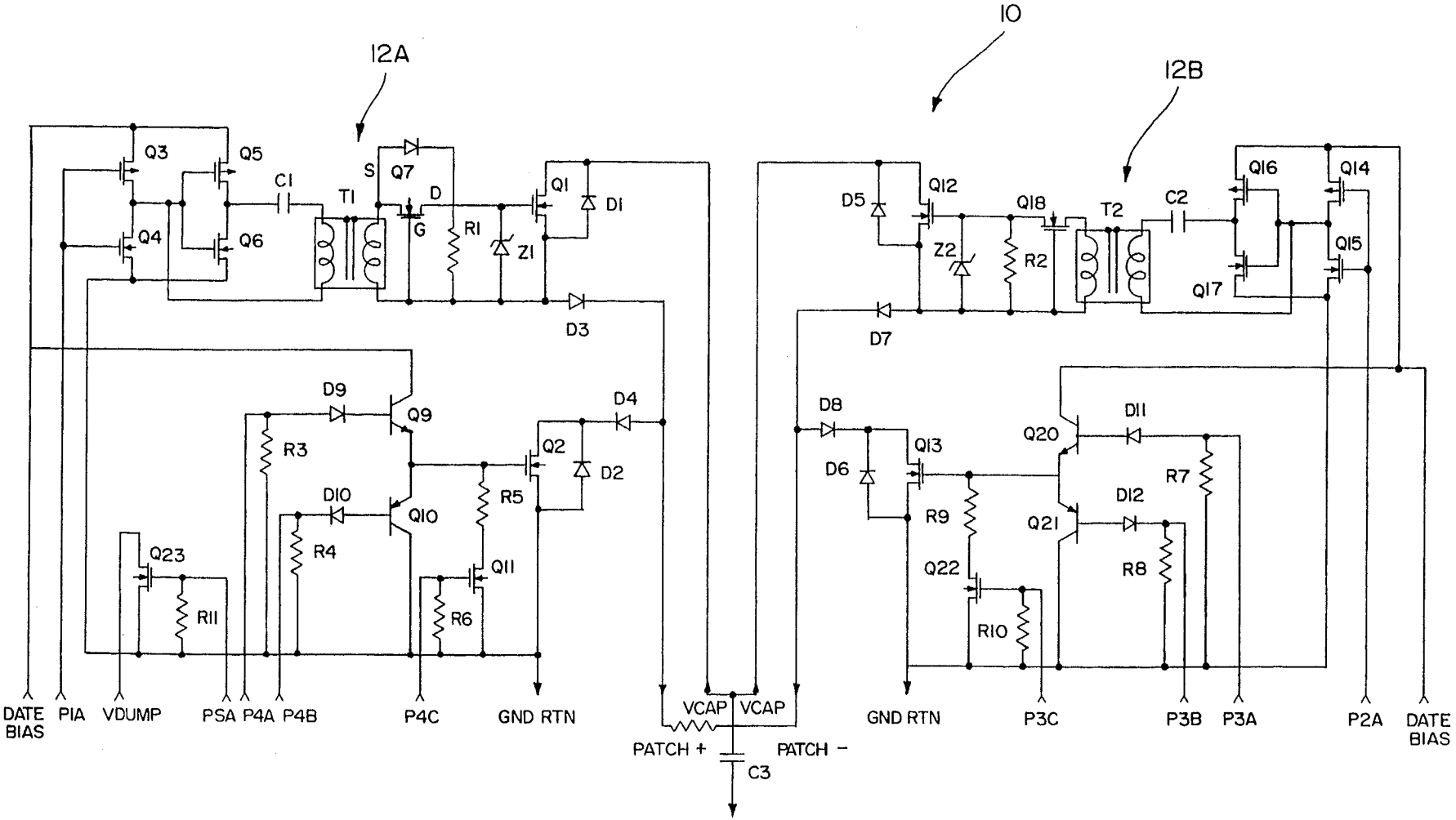
FIG. 1 is an electrical schematic diagram of the implanatable defibrillator output bridge circuit in accordance with the present invention.

Referring first to FIG. 1, the implantable defibrillator output bridge circuit is generally shown at 10. The circuit 10 comprises a left portion 12a and a right portion 12b. With the exception of the transistor Q23 and resistor R11, the circuit portions 12a and 12b are mirror images of each other. Therefore, a detailed description of circuit portion 12a will be made first and a brief description of circuit portion 12b will follow.

The circuit 10 includes input signal pins P1A, P2A, P3A, P4A, P5A, P3B, P4B, P3C, and P4C. In addition, output pins are provided at patch+and patch−for connecting the circuit 10 to defibrillation electrodes implanted on the heart. Ground return pins are also provided for each side of the circuit 10, the function of which will be described hereinafter. Each circuit portion 12a and 12b connects to a capacitor C3 at respective pins designated Vcap. The four MOSIGT's are transistors Q1, Q2, Q12, and Q13. The top transistors Q1 and Q12 have transformer isolated gate drives. The bottom transistors Q2 and Q13 have controlled turn off time and low impedance clamping. Each MOSIGT Q1, Q2, Q12, and Q13 has independent on/off control. As will become more apparent hereinafter, transistors Q1 and Q12 are used for controlling the multi-phasic nature of the defibrillation pulse, while transistors Q2 and Q13 set the polarity of the defibrillation pulse by selecting one of the pins patch+or patch−as the ground-return.

Input signal pin P1A connects to push-pull driver transistor configuration comprising transistors Q3, Q4, Q5, and Q6. The push-pull driver generates a square wave with amplitude +/−Gate-bias. The push-pull driver is connected to a DC blocking capacitor C1, which in turn is connected to the primary side of the pulse transformer T1. The gate and source of the transistor Q7 connects across the secondary side of the transformer T1 while the gate and drain of Q7 are connected in parallel with resistor R1 and zener diode Z1. The gate and source of the transistor Q1 are connected in parallel with resistor R1 and zener diode Z1. Diode D1 connects across the drain and source of the transistor Q1.

Diodes D3 and D4 connect the source of transistor Q1 to the drain of transistor Q2. Diode D2 connects across the source and drain of the transistor Q2. The gate of the transistor Q2 is connected to resistor R5 and the emitters of the transistors Q9 and Q10. Resistor R5 also connects to the drain of the transistor Q11. Connected across the gate and source of transistor Q11 is resistor R6.

A series connection of resistor R3 and diode D9 is connected to the base of the transistor Q9. Similarly, the series connection of resistor R4 and diode D10 is connected to the base of the transistor Q10. Input signal pins P4A and P4B connect between resistor R3 and diode D9, and resistor R4 and diode D10, respectively. Transistors Q23 is provided with resistor R11 connected across its gate and source for providing access to an external dump load as will be explained hereinafter.

The circuit portion 12b is the same as circuit portion 12a with the exception of transistor Q23 and resistor R11. Transistors Q14, Q15, Q16, and Q17 comprise a push-pull driver configuration connected to the pulse transformer T2 in the same way as transistors Q3–Q6. Transistor Q18 is connected to the secondary side of the transformer T2 and to resistor R2, zener diode Z2, and transistor Q12, similar to the connections between transistor Q7, resistor R1, zener diode Z1 and transistor Q1 in circuit portion 12a.

Diodes D7 and D8 connect the transistor Q1 to the transistor Q13 in a similar manner as diodes D3 and D4 connect transistor Q1 to transistor Q2. The gate of transistor Q13 connects to the emitters of transistors Q20 and Q21 and to resistor R9. The series connection of resistor R7 and diode D11 is connected to the base of the transistor Q20. Similarly, the series connection of diode D12 and resistor R8 is connected to the base of transistor Q21. The input signal control pins P3A and P3B connect between resistor R7 and diode D11, and resistor R8 and diode D12, respectively. Resistor R9 connects the emitters of the transistors Q20 and Q21 to the drain of the transistor Q22. Resistor R10 is connected across the gate and source of transistor Q22.

The operation of circuit 10 will now be described with respect to the transistor Q1 and Q13 corresponding to input signal pins P1A, and P3A, P3B, and P3C, respectively, while pins P4A, P4B, P2A and P4C are at ground potential. The Gate-bias voltage is positive with respect to ground-return. To operate transistor Q1, a positive going pulse with respect to the ground-return is applied to pin P1A. This drives the push-pull driver configuration of transistors Q3–Q6 to generate a square wave with amplitude +/−Gate-bias. This drives the primary side of the pulse transformer T1 via the DC blocking capacitor C1. A positive pulse on the dotted secondary of the pulse transformer T1 causes the intrinsic body diode, created by making the gate more negative than the source, to conduct, which then causes the gate of transistor Q1 to charge to+Gate-bias volts, turning transistor Q1 on. As long as a positive voltage pulse is applied on pin P1A, transistor Q1 is on until the gate charge is depleted. A negative pulse on the secondary of pulse transformer T1 caused by pin P1A returning to ground potential forces the gate of the transistor Q7 to be more positive than the source of transistor Q7, so that transistor Q7 turns on providing a low impedance discharge path for the gate charge on transistor Q1. Hence, Q1 turns off. The zener diode Z1, when forward biased, prevents the gate of transistors Q1 from charging to −Gate-bias volts. The overall impedance that the gate of transistor Q1 sees when charging or discharging is the output impedance of the push-pull driver configuration of transistors Q3–Q6. Resistor R1 provides a high impedance gate discharge path, gate to source, of transistor Q1, that prevents charge from accumulating on the gate of transistor Q1 and therefore prevents false turn on. The zener diode Z1 clamps positive gate to source voltage of transistor Q1 in excess of positive gate-bias that may be caused via the transfer capacitance of transistor Q1 by rapidly changing positive drain to source voltages. Zener diode Z1 also clamps negative gate to source voltages in excess of a diode drop caused by the same conditions. Further, zener diode Z1 protects the gate to source potential of transistor Q1 from exceeding its maximum ratings and also helps to minimize false turn on caused by a change of voltage with respect to time seen by the drain to source of transistor Q1.

Diode D1 protects Q1 if the source potential is greater than drain potential. Diode D3 also protects Q1 in an effort to keep current from flowing into the source of Q1 if the cathode side of diode D3 becomes more positive than the drain of transistor Q1. This condition can occur due to the stray inductance and the counter EMF generated by the change in current with respect to time when the other side of the bridge is turned off. Diodes D6 and D8 protect transistor Q13 in the same way as diodes D1 and D3 protect transistor Q1.

To operate transistor Q13, input signal pins P3A, P3B, and P3C are employed. A positive going pulse with respect to ground-return on pins P3A and P3B turns on transistor Q20, and turns off transistor Q21, respectively, which then allows the gate of transistor Q13 to charge to+Gate-bias volts, thus turning transistor Q13 on. The input signal at pin P3C must be kept low to keep transistor Q13 on. When pin P3A is set low, Q20 is turned off. P3C is set high while P3B is still high to turn on transistor Q22. Thus, the gate of transistor Q13 slowly discharges through resistor R9. By allowing the gate to slowly discharge, the drain current through transistor Q13 slowly decreases thereby reducing the change with respect to time of the drain current. The input signal at pin P3B was positive and returns to ground-return. This turns on transistor Q21 to provide a low impedance clamp to the gate of transistor Q13, thus turning transistor Q13 off. Once pin P3B is set low, P3C can be set low. A low impedance clamp is required to prevent transistor Q13 from falsely turning on due to induced gate voltages caused by rapidly changing positive drain to source voltages that couple through the transfer capacitor. Resistors R7, R8, and R10 are pull down resistors to keep transistors Q20, and Q22 off, and Q21 on for activating the low impedance clamp. The diodes D11 and D12 protect the base to emitter junctions of transistors Q20 and Q21, respectively. Diodes D11 and D12 also prevent the base to emitter junctions of these transistors from entering the zener conduction region when transistor Q20 is off but there is still a +Gate-bias voltage on the gate of transistor Q13, and when transistor Q20 is on but transistor Q21 is off.

Because the bridge is symmetrical, the same operation applies to the transistors Q2 and Q12. Specifically, a positive going pulse with respect to ground-return applied to pin P2A turns on transistor Q12 via the push-pull driver configuration of transistors Q14–Q17 and the transformer T2.

A positive going pulse on pins P4A and P4B turns on transistor Q2 by turning on transistor Q9 and turning off transistor Q10, respectively. Pin P4C is held at ground potential to keep Q2 turned on. A pulse on pin P4B turns on transistor Q10 and thus provides a low impedance clamp to the gate of transistor Q2, turning Q2 off. Diodes D9 and D10 function in the same way as diodes D11 and D12.

In the event that the defibrillation pulse should not be delivered to the heart, pin P5A is set high to direct the pulse to an external load (not shown).

Figure 2:
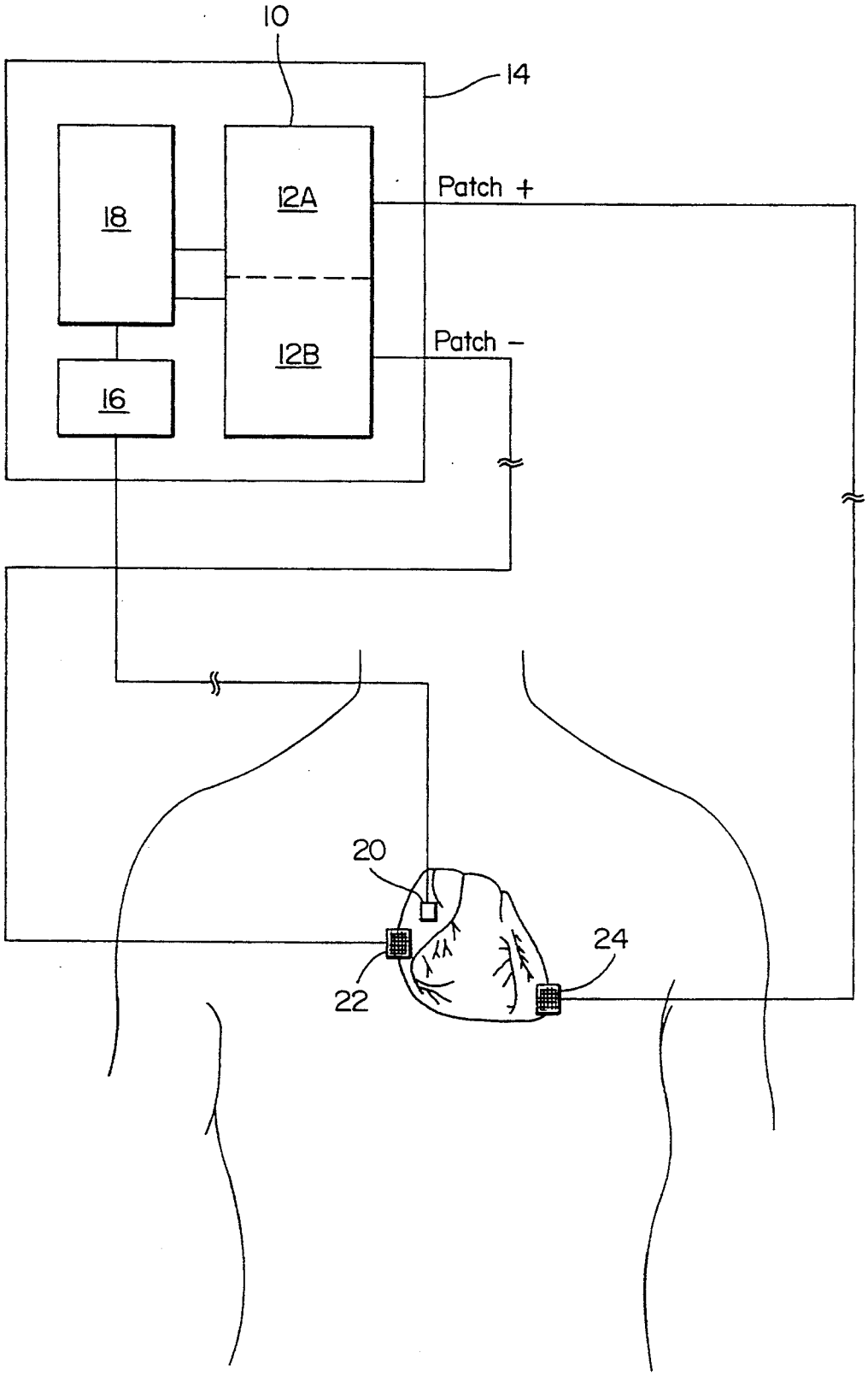
FIG. 2 is a schematic diagram illustrating the use of the implantable defibrillator output bridge circuit of the present invention in conjunction with an implanatable defibrillation system.

The circuit 10 is used in an implantable defibrillator unit 14 as part of an implantable defibrillation system illustrated in FIG. 2. Typically, the defibrillator unit 14 also includes an arrhythmia detection circuit 16 and a stimulation control circuit 18 connected to both the detection circuit 16 and the output circuit 10. Defibrillator unit 14, including the circuits 10, 16, and 18, is of a size whereby it comfortably can be implanted in the abdomen of the patient.

The arrhythmia detection circuit 1 is connected to sensing electrodes 20 implanted in or on the heart. The output circuit 10 is connected to implanted electrodes 22 and 24, shown mounted on the heart for performing defibrillation. The control circuit 18 is triggered by the arrhythmia detection circuit 16 to trigger the output circuit 10 and apply a defibrillation pulse to the heart across electrodes 22 and 24. The output circuit 10 is capable of delivering mono-phasic, bi-phasic, tri-phasic, . . . n-phasic, and sequential defibrillation pulses to the heart depending upon the control signals applied to the input signal pins P1A–P5A, P3B, P4B, P3C and P4C. The desired type of defibrillation pulse delivered to the heart is programmed in the control circuit 18 which applies the necessary signals to the appropriate signal pins.

As mentioned previously, transistors Q1 and Q12 determine the multi-phasic nature of the defibrillation pulse, and transistors Q2 and Q13 determine the polarity of the pulse. Transistors Q1 and Q13 are used together to generate positive pulses. Transistors Q2 and Q12 are used together to generate negative pulses. With transistor Q!3 turned on, positive pulses will be generated, the duration of which is determined by the length of time transistor Q1 is turned on. The same is true for negative pulses generated by maintaining transistor Q2 on, and varying the pulse duration by the duration which transistor Q12 is on. To generate multi-phasic pulses, the activation of transistors Q1 and Q13 is followed by the activation of transistors Q2 and Q12, or vice versa, for as many phases of the pulse desired. The actual pulse, whether positive or negative, exponentially decreases in magnitude as it normally would, across capacitor C3.

With reference to FIGS. 1 and 3a–3h, representative defibrillation pulses which can be delivered to the heart by the output circuit 10 will now be described.

Figure 3A:
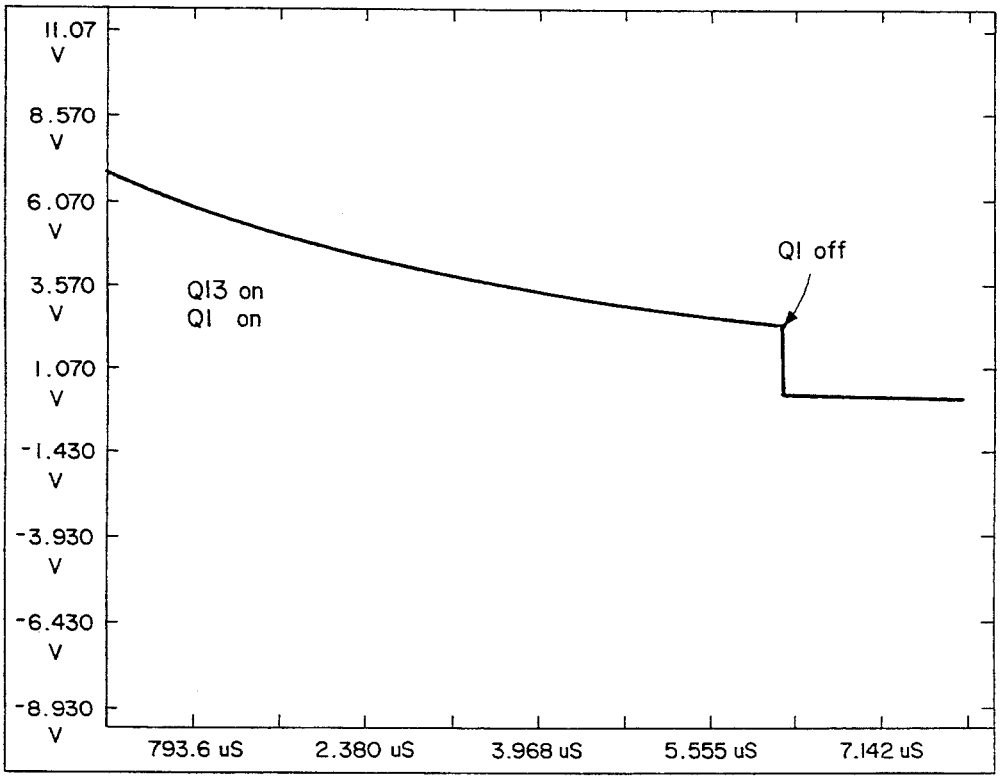
FIGS. 3a–3h are graphical plots of defibrillation pulses produced by the output bridge circuit illustrated in FIG. 1.

FIG. 3a illustrates a mono-phasic pulse with positive polarity. To achieve this pulse, input signal pins P3A and P3B are set high and input signal pin P3C is grounded to turn transistor Q13 on. A positive going pulse of a predetermined duration is then obtained by setting pin P1A high to turn on transistor Q1.

Figure 3B:
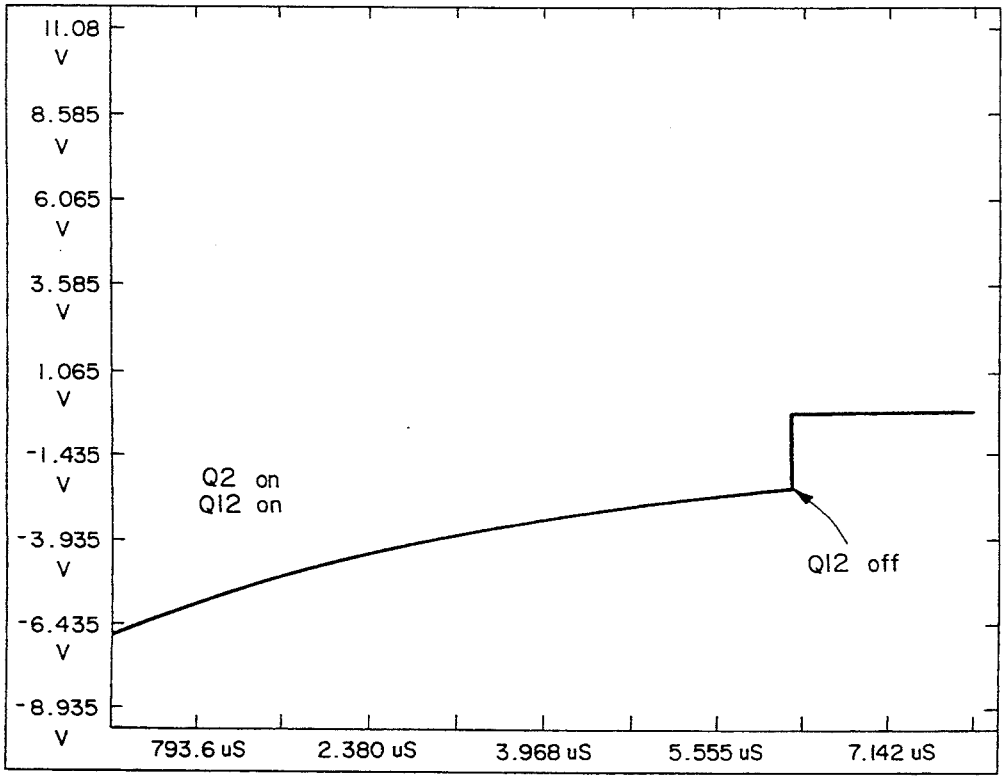

FIG. 3b illustrates a mono-phasic pulse with negative polarity. This is achieved by setting pins P4A and P4B high and setting pin P4C low to turn on transistor Q2. A pulse is then applied to pin P2A to turn on transistor Q12.

Figure 3C:
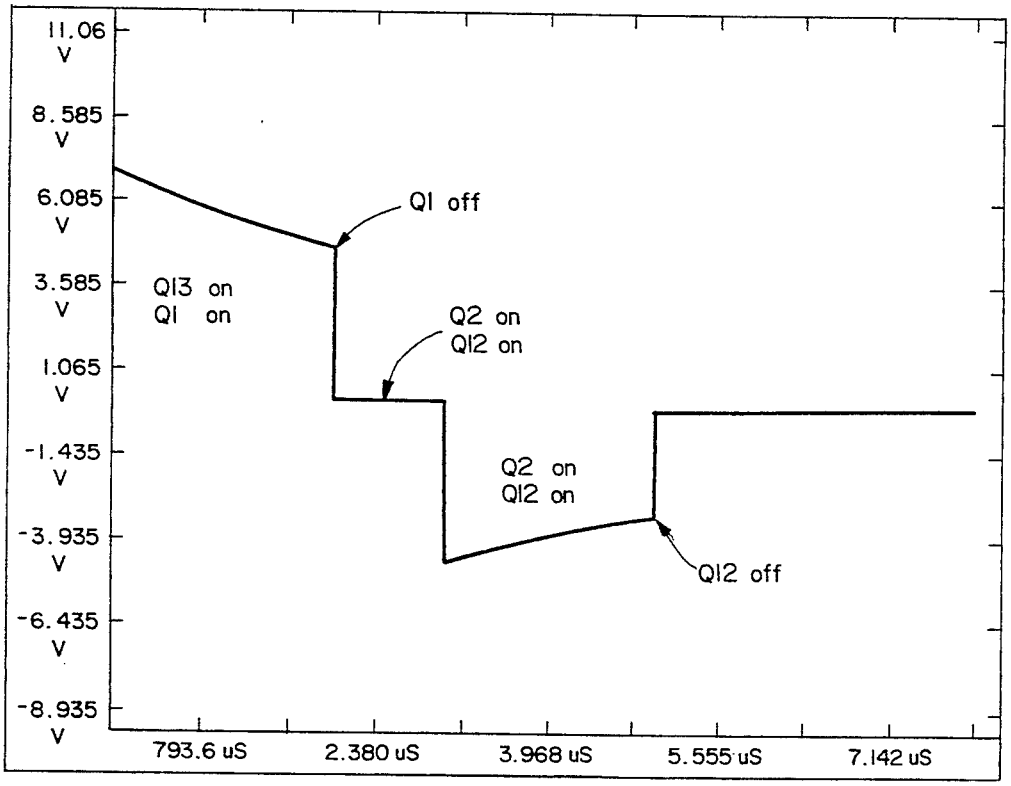

FIG. 3c illustrates a bi-phasic pulse with positive polarity achieved by setting pin P3A and pin P3B high and setting pin P3C low. A pulse is applied to pin P1A, turning transistor Q1 on. Thereafter, pin P4A and pin P4B are set high and pin P4C is set low to turn on transistor Q2. A pulse is then applied to pin P2A to turn on transistor Q12.

Figure 3D:
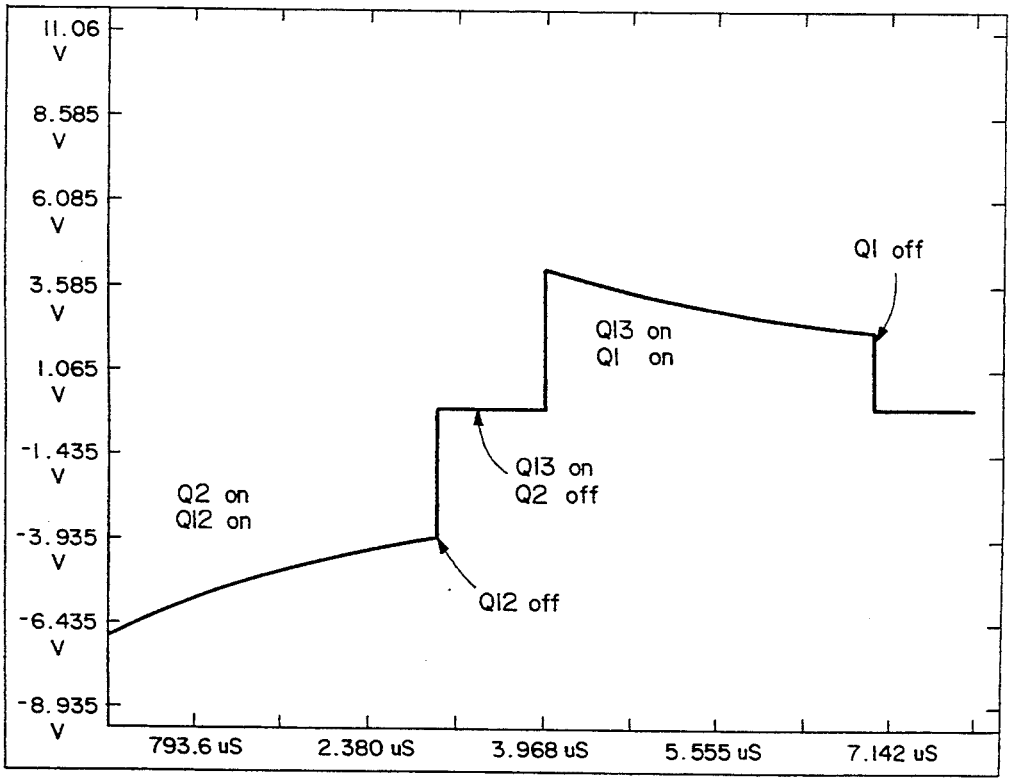

FIG. 3d illustrates a bi-phasic pulse with negative polarity achieved by setting pin P4A and pin P4B high and setting pin P4C low. This turns on transistor Q2. A pulse is then applied to pin P2A, turning on transistor Q12. This creates the negative portion of the bi-phasic pulse. Thereafter, pins P3A and P3B are set high and pin P3C is set low, and a pulse is applied to pin P!A. This turns on transistors Q13 and Q1 to create the positive portion of the bi-phasic pulse.

Figure 3E:
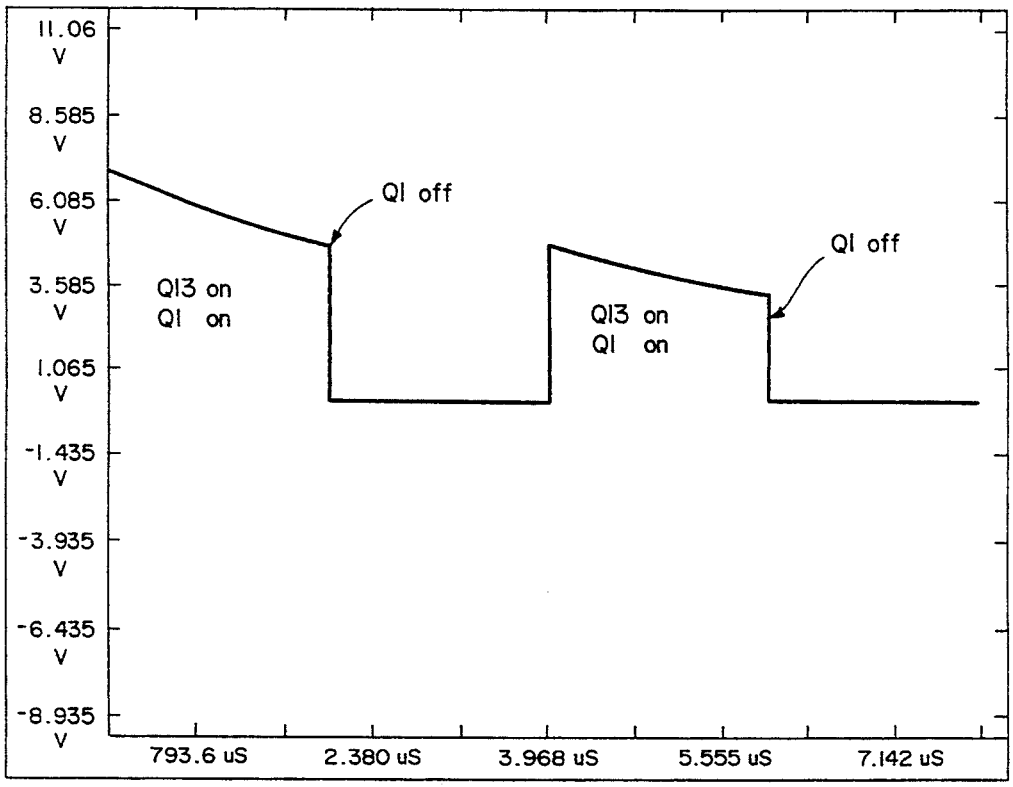

FIG. 3e illustrates sequential pulses with positive polarity. This is achieved by setting pin P3A and pin P3B high and setting pin P3C low to turn on transistor Q13. A pulse is then applied to pin P1A, turning transistor Q1 on, and repeated for as many positive pulses needed.

Figure 3F:
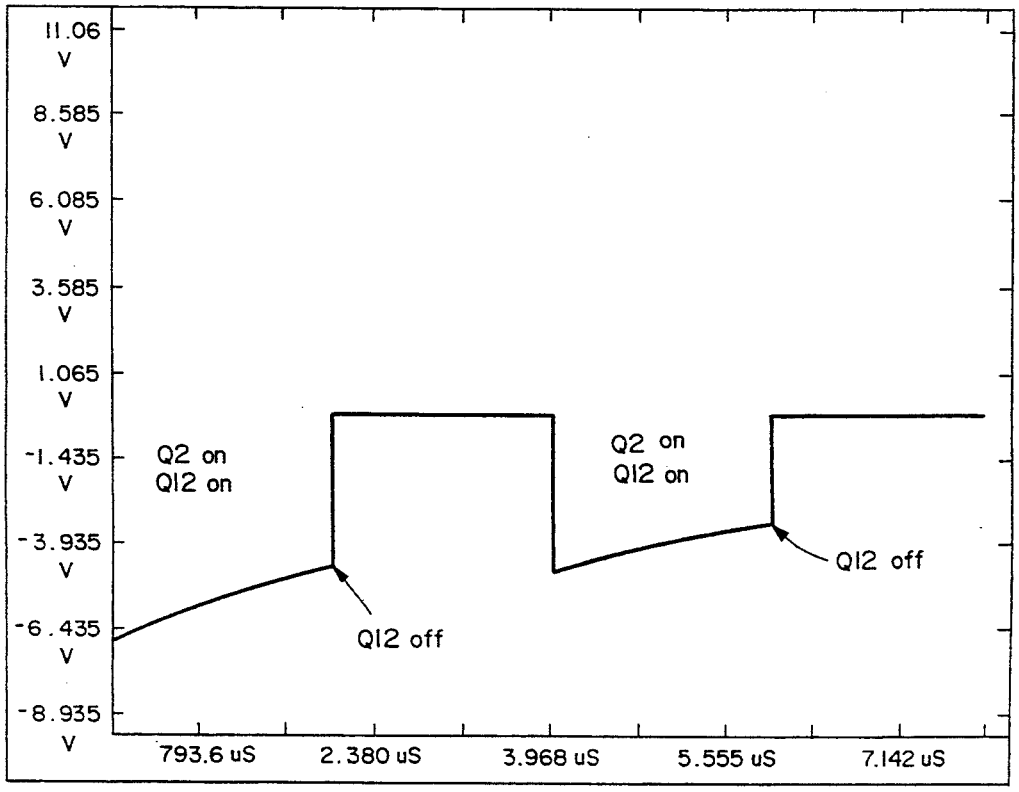

FIG. 3f illustrates sequential pulses with negative polarity being achieved by setting pins P4A and P4B high and setting pin P4C low to turn on transistor Q2. Repeated pulses are applied to pin P2A to turn on transistor Q12 for as many negative pulses desired. As seen in FIGS. 3e and 3f, no voltage is lost across capacitor C3.

Figure 3G:
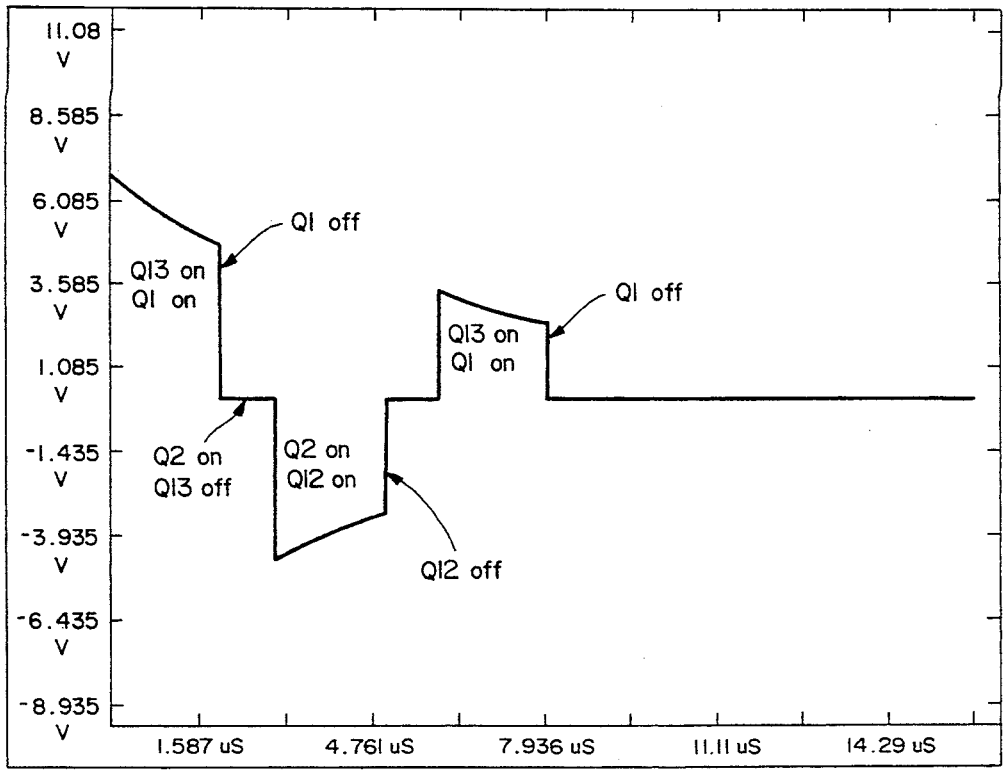

FIG. 3g illustrates a tri-phasic pulse with positive polarity. This is achieved by first setting pin P3A and pin P3B high and setting pin P3C low. A pulse is then applied to pin P1A. Then, pins P4A and P4B are set high and pin P4C set low. A pulse is then applied to pin P2A. Finally, pins P3A and P3B are set high and pin P3C is set low. A pulse is applied to pin P1A.

Figure 3H:
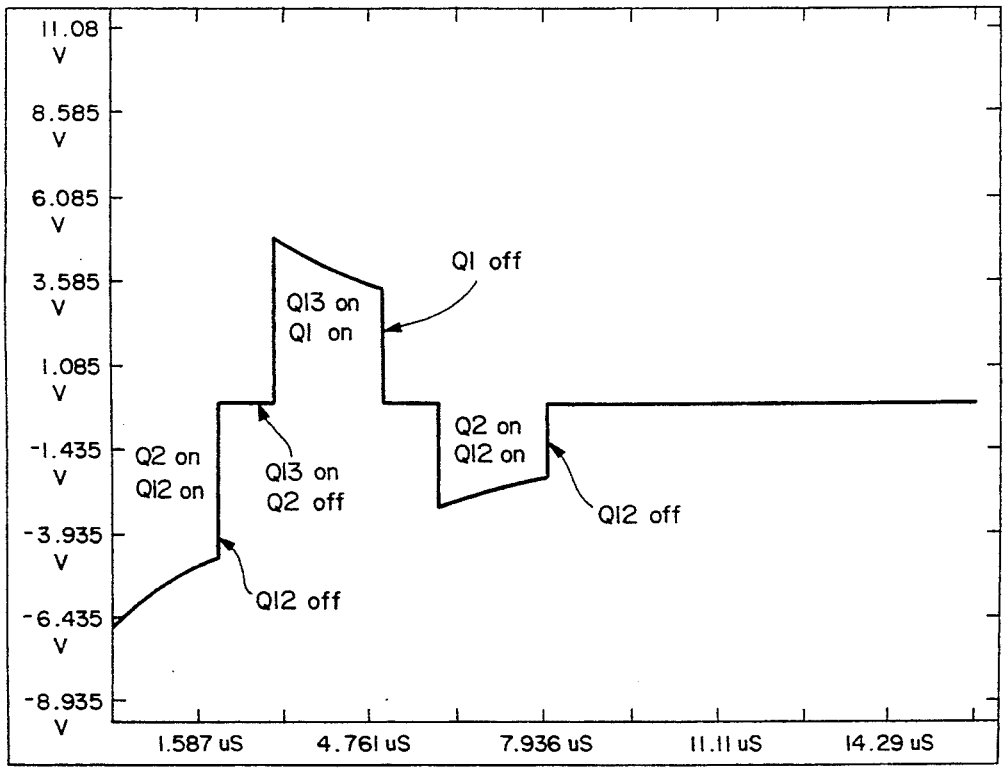

FIG. 3h illustrates a tri-phasic pulse with negative polarity. This is achieved by first setting pins P4A and P4B high and setting pin P4C low. A pulse is applied to pin P2A. Then, pins P3A and P3B are set high and pin P3C is set low. A pulse is applied to pin P1A. Finally, pins P4A and P4B are set high and pin P4C is set low. A pulse is then applied to pin P2A.

Energy flow is always from Vcap, through transistor Q1, out through patch+, through the heart, into patch−, through transistor Q13, to ground-return, or from Vcap, through transistor Q12, out through patch−, through the heart, into path+, through transistor Q2, and to ground-return.

The advantages of this output bridge circuit are the independent on/off controls of transistors Q1, Q2, Q12, and Q13. The three control pins P4A, P4B, P4C, and P3A, P3B, and P3C for the gate drive circuits of transistors Q2 and Q13, respectively, allow separate control to turn on and off, and reduce current variations with respect to time. In operation, at least one of the two patch leads path+or patch−is always connected to ground-return. Furthermore, a n-phasic defibrillation pulse can easily be generated by alternating the activation of transistors Q1 and Q13 together, with the activation of transistors Q2 and Q12 together.

The above description is intended by way of example only and is not intended to limit the present invention in any way except as set forth in the following claims.

We claim:

1. An output circuit for use in an implantable defibrillation system, said circuit comprising:

capacitor means for storing a predetermined voltage;

first and second switching means, both connected to said capacitor means and capable of being triggered to active conditions;

a ground-return terminal;

first and second electrode lead terminals connected to said first and second switching means, respectively;

[third and] fourth *and third* switching means connected to said first and second lead terminals, respectively, for selectively connecting said first and second electrode lead terminals, respectively, to said ground-return terminal when triggered to active conditions; and triggering means for triggering said first and said third switching means to said active conditions to allow voltage stored by said capacitor means to discharge through said first and second electrode lead terminals in a first polarity, and for triggering said second and fourth switching means to said active conditions to allow voltage stored by said capacitor means to discharge through said first and second electrode lead terminals in a second polarity opposite to said first polarity.

2. The circuit of claim 1, and further comprising first and second push-pull driver circuits; first and second control pins connected to said first and second push-pull driver circuits, respectively; and first and second pulse transformers; said first and second pulse transformers including primary and secondary windings, said secondary windings being connected to said first and second switching means, said primary windings being connected to said push-pull driver circuits, and said first and second switching means being triggered to said active conditions by applying an electrical pulse to said first and second control pins.

3. An implantable defibrillation system for delivering mono-phasic, multi-phasic, and sequential defibrillation pulses to a heart via a pair of electrodes implanted on or about the heart, said system comprising:

an output circuit comprising capacitor means for storing a predetermined voltage, first and second switching means both connected to said capacitor means and capable of being triggered to active conditions;

a ground return terminal;

first and second electrode lead terminals connected, respectively to said first and second switching means and to said pair of electrodes;

[third and] fourth *and third* switching means for selectively connecting said first and second electrode lead terminals, respectively, to said ground return terminal when triggered to active conditions;

a control circuit for selectively triggering said first and said third switching means to said active conditions for allowing voltage stored by said capacitor means to discharge through said first and second electrode lead terminals in a first polarity, and triggering said second and fourth switching means to said active conditions for allowing voltage stored by said capacitor means to discharge through said first and second electrode lead terminals in a second polarity opposite to said first polarity.

4. A method for generating a multi-phasic defibrillation pulse via four independently controlled electrical switching elements for delivery to the heart of a patient via first and second electrodes implanted on or about the heart, said method comprising the steps of:

charging a capacitor to a predetermined voltage;

triggering a first electrical switching element connected to said capacitor and said first electrode to an active condition and triggering a third electrical switching element connected to said second electrode and a ground terminal to an active condition for delivering voltage through said first an second electrodes to the heart in a first polarity;

triggering a second electrical switching element connected to said capacitor and said second electrode to an active condition and triggering a fourth electrical switching element connected to said first electrode and a ground terminal to an active condition for delivering voltage through said first and second electrodes to the heart in a second polarity opposite to said first polarity.

5. An implantable defibrillation system for delivering mono-phasic, multi-phasic and sequential defibrillation pulses to a heart via a pair of discharge electrodes implanted on or about the heart, said system comprising:

sensing electrode means mounted on or about the heart;

arrhythmia sensing means connected to said sensing electrode means for detecting an arrhythmia of the heart;

an output circuit comprising capacitor means for storing a predetermined voltage; first and second switching means connected to said capacitor means and said discharge electrodes, and capable of being triggered to active conditions; a ground return terminal; first and second electrode lead terminals connected, respectively, to said first and second switching means and to said pair of electrodes; [third and] fourth *and third* switching means for selectively connecting said first and second electrode lead terminals, respectively, to said ground return terminal when triggered to active conditions;

control means for selectively triggering said first and said third switching means to said active conditions for allowing voltage stored by said capacitor means to discharge through said first and second electrode lead terminals in a first polarity, and triggering said second and fourth switching means to said active conditions for allowing voltage stored by said capacitor means to discharge through said first and second electrode lead terminals in a second polarity opposite to said first polarity.

* * * * *